US006612996B2

(12) United States Patent
Williams

(10) Patent No.: US 6,612,996 B2
(45) Date of Patent: Sep. 2, 2003

(54) CERVICAL SAMPLER FOR PAP SMEARS

(76) Inventor: Donald Williams, 1320 Santiago Dr., Newport Beach, CA (US) 92660

(*) Notice: Subject to any disclaimer, the term of this patent is extended or adjusted under 35 U.S.C. 154(b) by 0 days.

(21) Appl. No.: 09/888,334

(22) Filed: Jun. 22, 2001

(65) Prior Publication Data

US 2002/0016556 A1 Feb. 7, 2002

Related U.S. Application Data

(60) Provisional application No. 60/213,792, filed on Jun. 23, 2000.

(51) Int. Cl.[7] ............................................. A61B 10/00
(52) U.S. Cl. .................................. 600/569; 600/562
(58) Field of Search ........................... 600/569, 300, 600/562, 570, 572

(56) References Cited

U.S. PATENT DOCUMENTS

| 3,881,464 A | * | 5/1975 | Levene ..................... 600/569 |
| 5,191,899 A | * | 3/1993 | Strickland et al. ........... 600/569 |
| 5,456,265 A | * | 10/1995 | Yim .......................... 600/569 |
| 5,623,941 A | * | 4/1997 | Hedberg et al. ............. 600/569 |
| 6,336,905 B1 | * | 1/2002 | Colaianni ................... 600/569 |

* cited by examiner

Primary Examiner—Thor Campbell
(74) Attorney, Agent, or Firm—Knobbe, Martens, Olson & Bear

(57) ABSTRACT

A cervical sampler for insertion into the cervical canal of a patient comprises an elongated shaft having a proximal end and a distal end, a brush disposed on the distal end, and a cannula slidably positioned on the shaft. The cannula is moveable between a first position in which the cannula covers the brush and reduces the insertion profile of the cervical sampler, and a second position in which the cannula exposes the brush for operative contact with the cervical canal. There is also disclosed a method of obtaining sample tissue from the cervical canal of a patient with a sampling brush having a shaft and a bristled portion on the shaft. The method comprises covering the bristled portion of the sampling brush by sliding a sheath distally along the shaft and over the bristled portion and inserting the sampling brush into the cervical canal until the bristled portion, covered by the sheath, is disposed within the cervical canal. The method further comprises sliding the sheath proximally along the shaft to expose the bristled portion to operative contact with the cervical canal, and advancing the bristled portion proximally within the cervical canal to collect sample tissue from the cervical canal upon the bristled portion.

26 Claims, 5 Drawing Sheets

CERVICAL SAMPLER FOR PAP SMEARS

CROSS REFERENCE TO RELATED APPLICATION

This Application claims the benefit under §119(e) of Provisional Application No. 60/213,792, filed Jun. 23, 2000.

BACKGROUND OF THE INVENTION

1. Field of the Invention

The present invention relates to cervical sampling devices for retrieval of cellular material from within the cervical canal of a patient.

2. Description of the Related Art

A Pap smear is a routine procedure performed on female patients to screen for cervical cancer. The procedure involves retrieval of exfoliative cellular material from within the cervical canal for subsequent examination for the presence of cancerous material. It is well known to use a sampler in the form of a long-handled brush to collect the material of interest. The brush is inserted through the vaginal opening and into the cervical canal, where the bristles of the brush collect a sample of the cellular material of interest from the cervical walls. Upon withdrawal of the brush, the collected cellular material is transferred from the brush onto a slide or into a liquid fixative for examination.

Existing brush systems have various drawbacks which may be addressed through the development and use of an improved cervical sampler.

SUMMARY OF THE INVENTION

In accordance with one aspect of the invention a cervical sampler for insertion into the cervical canal of a patient comprises an elongated shaft having a proximal end and a distal end, a brush disposed on the distal end, and a cannula slidably positioned on the shaft. The cannula is moveable between a first position in which the cannula covers the brush and reduces the insertion profile of the cervical sampler, and a second position in which the cannula exposes the brush for operative contact with the cervical canal. In accordance with another aspect of the invention there is provided a method of obtaining sample tissue from the cervical canal of a patient with a sampling brush having a shaft and a bristled portion on the shaft. The method comprises covering the bristled portion of the sampling brush by sliding a sheath distally along the shaft and over the bristled portion and inserting the sampling brush into the cervical canal until the bristled portion, covered by the sheath, is disposed within the cervical canal. The method further comprises sliding the sheath proximally along the shaft to expose the bristled portion to operative contact with the cervical canal, and advancing the bristled portion proximally within the cervical canal to collect sample tissue from the cervical canal upon the bristled portion.

In accordance with yet another aspect of the invention, a cervical sampler comprises a brush assembly comprising an elongated shaft and a bristled portion at a distal end of the shaft, and a sheath slidably disposed on the shaft. The sheath has a first position in which the sheath covers and compresses the bristled portion to reduce the insertion profile of the cervical sampler, and a second position in which the sheath exposes the bristled portion and permits the bristled portion to return to an uncompressed state.

These and other aspects of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which.

DETAILED DESCRIPTION OF THE PREFERRED EMBODIMENT

Figure 1A:
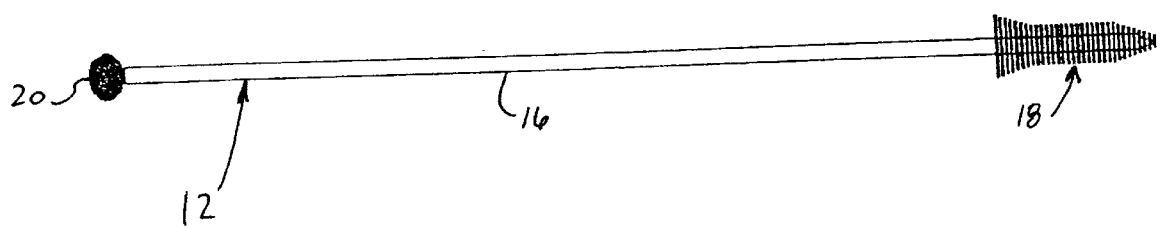
FIG. 1a is a side elevation view of a brush assembly portion of the cervical sampler.
Figure 1B:
FIG. 1b is a cross-sectional view of a cannula portion of the cervical sampler.

As shown in FIGS. 1a and 1b, the cervical sampler 10 comprises a cervical brush assembly 12 and a cannula or sheath 14. The brush assembly 12 comprises a shaft portion 16 which in the preferred embodiment measures about 17 cm in length and about 0.3 cm in diameter. A bristled portion or brush portion 18, which is substantially wider than the shaft portion 16, is mounted at the distal end of the shaft portion. In the preferred embodiment, the brush portion 18 measures about 2 cm in length and about 0.7 cm in diameter. A knob portion 20 is mounted at the proximal end of the shaft portion, and may, for example, measure 1.0 cm in diameter. The knob 20 provides a stop which halts distal to proximal movement of the cannula 14 at the proper position and provides a control point when using the cervical sampler 10. Of course, other suitable structure may be employed in providing a proximal cannula/sheath stop and/or handle for manipulating the sampler 10.

The cannula 14 comprises a tube having a lumen 22 therethrough. The diameter of the lumen 22 is slightly larger than the diameter of the shaft portion 16 of the brush assembly 12, but substantially smaller than the diameter of the brush portion 18. Additionally, the distal end 24 of the cannula 14 is tapered so as to avoid a blunt distal surface. The length of the cannula 14 is less than the length of the brush assembly 12. In particular, the cannula length is selected such that, when the proximal end 26 of the cannula is butted against the knob portion 20, the distal end 24 of the cannula 14 is adjacent and proximal to the brush portion 18, so that the entire brush portion 18 is exposed and distal to the cannula 14. In the preferred embodiment, the cannula measures about 16.5 cm in length and about 0.4 cm in external diameter. The cannula 14 may include a radially extending flange 28 which provides a stop for insertion of the cannula 14 into the cervical canal.

Figure 2A:
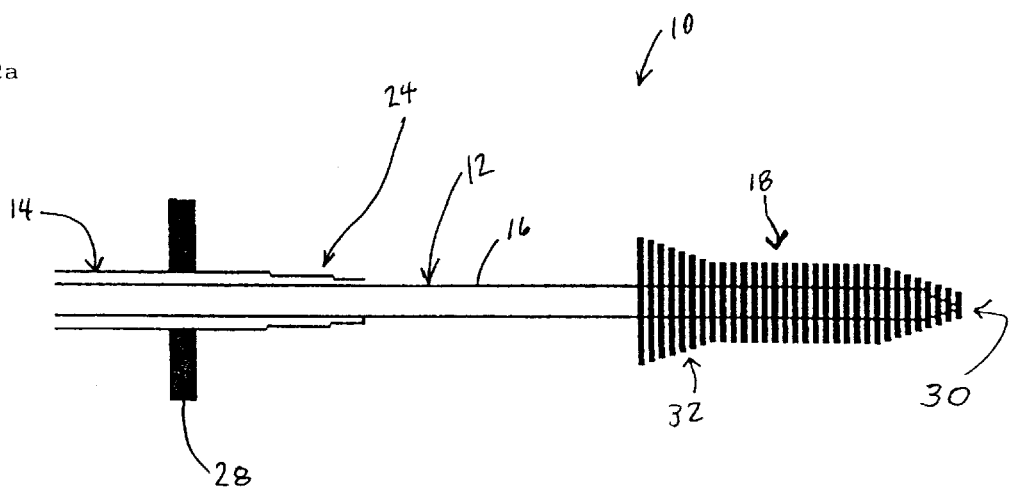
FIG. 2a is a detail, partial cross-sectional view of the distal half of the cervical sampler.
Figure 2B:
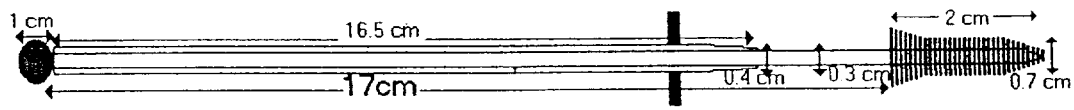
FIG. 2b is a partial side cross-sectional view of the inventive cervical sampler.

Referring to FIGS. 2a and 2b, the brush portion 18 of the cervical sampler 10 is comprised of nylon bristles, which are not alcohol soluble and have a melting point of greater than 200-degrees Fahrenheit. The brush portion 18 is preferably divided into two parts, an endocervical portion 30 and an ectocervical portion 32, for sampling the endocervical and ectocervical areas, respectively. The endocervical-sampling portion 30 is comprised of finer, softer, more flexible bristles than is a conventional cervical brush. Compared to the endocervical portion 30, the ectocervical portion 32 of the brush 18 is somewhat larger in diameter and slightly more rigid, having a consistency and density similar to the conventional rush. The bristles used in the brush 18 are soft and friable, are easily compressed by the distal portion of the cannula 14, and return to their original uncompressed state when the cannula 14 is withdrawn.

FIG. 2b shows the preferred approximate dimensions of the cervical sampler 10. It will be appreciated, however, that the cervical sampler encompasses variation from the dimensions shown in FIG. 2b and recited elsewhere herein, so long as the essential functions and advantages of the cervical sampler 10 are preserved.

Figure 3A:
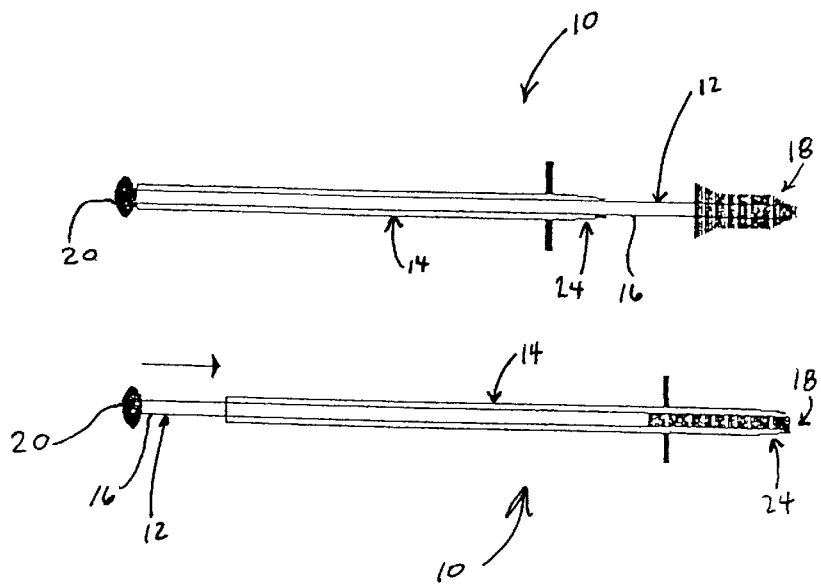
FIGS. 3a–3d and FIG. 4 are a series of schematic views of the cervical sampler as employed to retrieve cellular material from the cervix of a patient.

As shown in FIG. 3a, to operate the cervical sampler 10, the cannula 14 is pushed forward/distally until the distal end 24 of the cannula 14 is flush with the distal end of the brush portion 18, thereby compressing the brush portion 18.

Figure 3B:
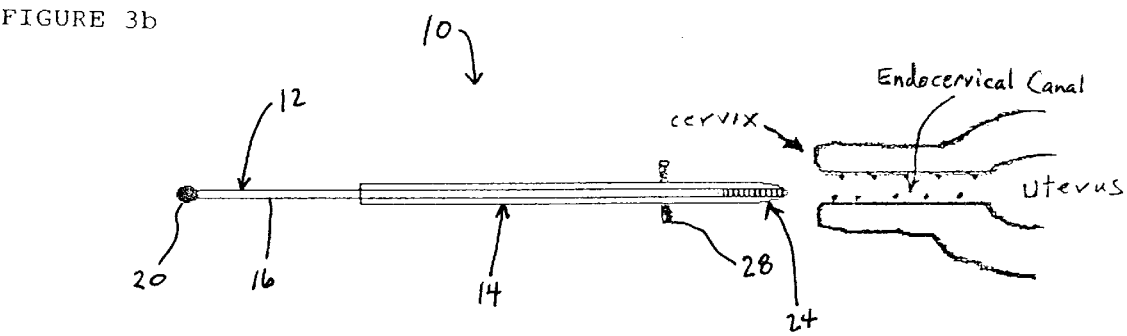
Figure 3C:
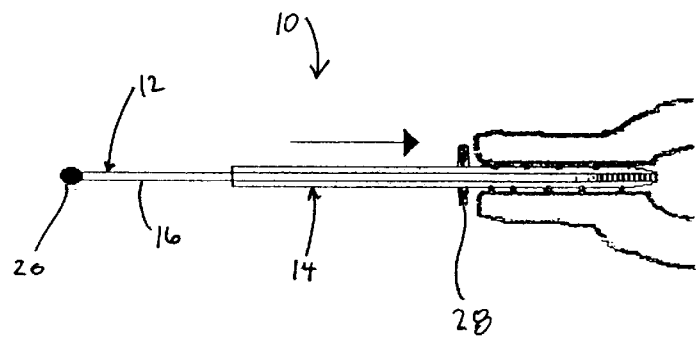

Referring to FIGS. 3b and 3c, the smooth, gradual taper on the distal end 24 of the cannula 14 allows the cervical sampler 10 to enter the endocervical canal without displacing exfoliative cellular material (represented by dots along the endocervical canal).

Figure 3D:
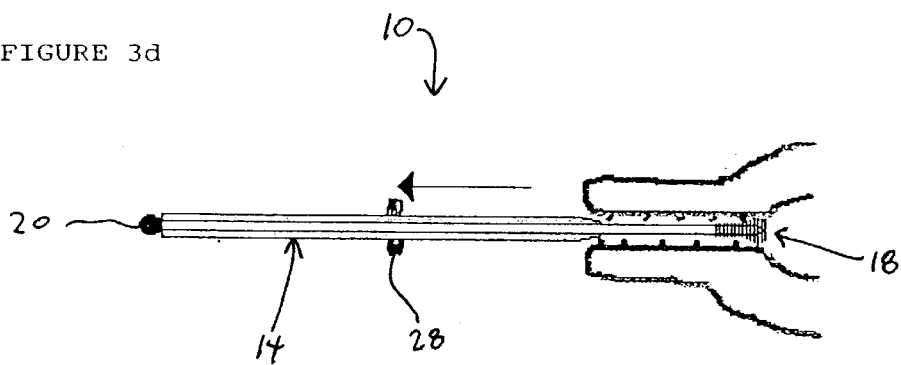

As shown in FIG. 3d, after the distal end of the cervical sampler 10 is positioned at the distal end of the canal, the cannula 14 is then withdrawn from the endocervical canal by pulling the cannula 14 proximally toward and against the knob portion 20, while the knob portion 20 is held stationary to prevent movement of the brush portion 18. Such withdrawal of the cannula 14 allows the brush portion to remain in place and expand within the canal from a compressed state to an uncompressed state in which bristles contact the walls of the canal.

Figure 4:
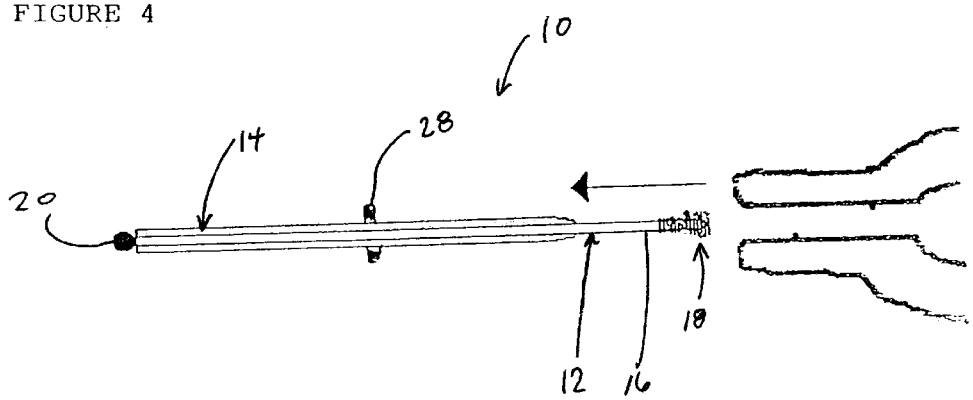

The entire cervical sampler 10 is then withdrawn from the canal. During such withdrawal of the cervical sampler 10, the proximal end of the cannula 14 preferably remains in contact with the knob 20, or otherwise disengaged from the brush portion 18. Such withdrawal causes the brush portion 18 to sweep the walls of the canal, taking with it substantially all exfoliative cellular material within the canal, as shown in FIG. 4.

Figure 5:
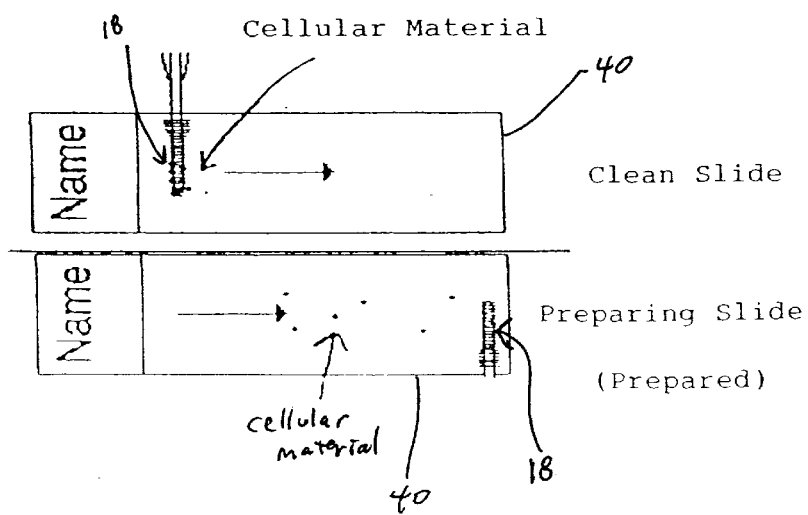
FIGS. 5 and 6 are schematic views of a method of transferring collected cellular material from the cervical sampler to a slide.

The exposed brush may then be "rolled" onto the bottom half of a glass slide 40 in the traditional manner, attempting to transfer as much cellular material from the brush portion 18 to the slide 40 as possible, as shown in FIG. 5.

Figure 6:
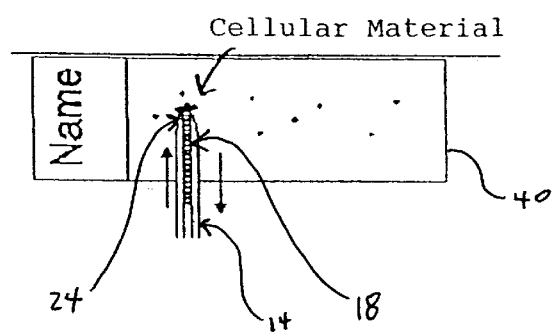

The cannula 14 is then moved relative to the brush portion 18 so that the distal end 24 of the cannula 14 is flush with the distal end of the brush portion 18, whereby the brush portion 18 is again compressed. Such compression forces the remaining cellular material to be expressed from the distal brush tip. As this material is expressed, it is transferred to the remaining half of the glass slide 40, as illustrated in FIG. 6.

Figure 7A:
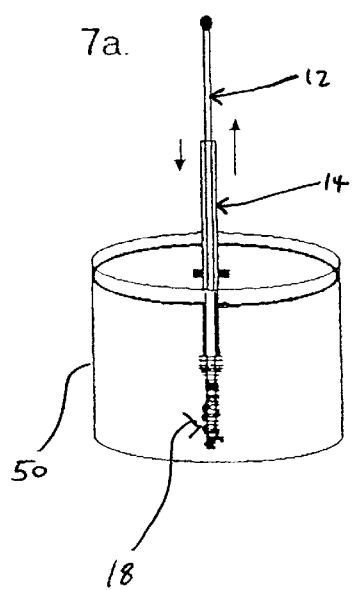
FIGS. 7a–7c are schematic views of a method of transferring collected cellular material from the cervical sampler to a liquid fixative.
Figure 7B:
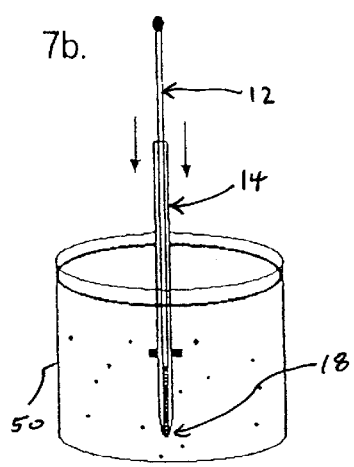
Figure 7C:
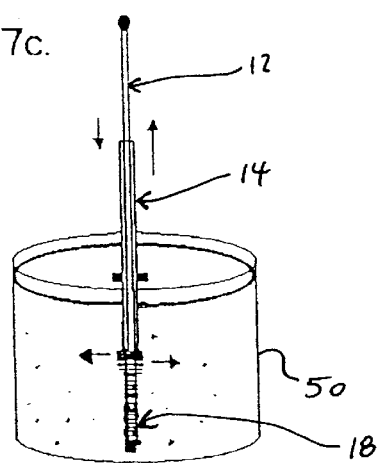

When the cervical sampler 10 is used for preparation of liquid-based Pap smear, the "rolling" of the brush portion 18 on the slide 40 is omitted. Once the sampler 10 is removed from the cervix, the exposed brush portion 18 is placed directly into a vial 50 containing liquid fixative. The cannula 14 is then moved forward covering the brush portion 18, and back again to expose the brush portion 18 to the liquid. This action of moving the cannula 14 back and forth is preferably repeated several times to gently wash all cellular material from the brush portion 18 into the liquid fixative, as illustrated in FIGS. 7a, 7b, and 7c.

From the foregoing, it will be appreciated that the disclosed cervical sampler provides significant advantages, among which include. First, the cervical sampler disclosed herein facilitates a higher yield of endocervical cells by greatly reducing the tendency of known brush systems to displace the exfoliative cellular material distally within the cervical canal during insertion of a "naked" brush (rather than pick up the material on the bristles), as well as by providing a way to transfer a higher proportion of the retrieved material onto a slide or into a liquid fixative. By ensuring a higher yield of endocervical cells, the inventive cervical sampler reduces the need for patients to return for re-testing, a frequent cause of complaints among patients. The disclosed cervical sampler also yields a greater amount of atypical cells, thereby achieving a better correlation rate. The cervical sampler described herein also removes a sample of cellular material which is more representative of the material in the cervix and endocervix, thus providing a higher-accuracy diagnosis of abnormalities. Finally, by minimizing contact with the brush, the cervical sampler reduces the pain and/or bleeding frequently experienced by patients when examined with known cervical samplers.

What is claimed is:

1. A cervical sampler for insertion into the cervical canal of a patient, said cervical sampler comprising:
    an elongated shaft having a proximal end and a distal end, and a brush disposed on said distal end; and
    a cannula slidably positioned on said shaft, said cannula being moveable between:
        a first position in which said cannula covers said brush; and
        a second position in which said cannula exposes said brush for operative contact with the cervical canal;
        wherein said brush is configured for ectocervical sampling such that a proximal portion of said brush has an outside diameter which is greater than that of a distal portion of said brush, at least said proximal portion outside diameter being greater than an inside diameter of said cannula.

2. The cervical sampler of claim 1, wherein said cannula has a tapered distal end.

3. The cervical sampler of claim 1, wherein said brush comprises a proximal ectocervical portion and a distal endocervical portion, said ectocervical portion having a larger average cross-sectional area than said endocervical portion.

4. The cervical sampler of claim 1, wherein said brush comprises a proximal ectocervical portion and a distal endocervical portion, said ectocervical portion having finer, softer bristles than said endocervical portion.

5. The cervical sampler of claim 1, further comprising a cannula stop located on said shaft proximal to said cannula.

6. The cervical sampler of claim 5, wherein said cannula stop comprises a handle.

7. The cervical sampler of claim 5, wherein said cannula stop comprises a knob.

8. A cervical sampler for insertion into the cervical canal of a patient, said cervical sampler comprising:
    an elongated shaft having a proximal end and a distal end, and a brush disposed on said distal end;
    a cannula slidably positioned on said shaft, said cannula being moveable between:

a first position in which said cannula covers said brush and reduces the insertion profile of said cervical sampler; and a second position in which said cannula exposes said brush for operative contact with the cervical canal; and a radially extending flange located on said cannula, said flange providing a stop for preventing over-insertion of said cervical sampler into the cervical canal.

9. The cervical sampler of claim 8, wherein said cannula has a tapered distal end.

10. The cervical sampler of claim 1, wherein said brush is tapered.

11. A method of obtaining sample tissue from the cervical canal of a patient with a sampling brush configured for ectocervical sampling, said brush having a shaft and a bristled portion on the shaft, said method comprising:

covering said bristled portion of said sampling brush by sliding a sheath distally along said shaft and over said bristled portion, said sheath having an inside diameter smaller than an outside diameter of an ectocervical portion of said bristled portion, so that said sheath compresses at least said ectocervical portion of said bristled portion against said shaft;

inserting said sampling brush into the cervical canal until said bristled portion, covered by said sheath, is disposed within the cervical canal;

sliding said sheath proximally along said shaft to expose said bristled portion to operative contact with the cervical canal; and advancing said bristled portion within the cervical canal to collect sample tissue from the cervical canal upon said bristled portion.

12. The method of claim 11, further comprising holding said shaft stationary while sliding said sheath proximally along said shaft.

13. The method of claim 11, wherein sliding a sheath distally along said shaft comprises sliding said sheath until a distal end of said sheath is flush with a distal end of said bristled portion.

14. The method of claim 11, further comprising:

placing said bristled portion in a container of liquid fixative; and sliding said sheath forward over said bristled portion to urge the sample tissue from said bristled portion and into said liquid fixative.

15. The method of claim 11, further comprising:

placing said bristled portion in a container of liquid fixative; and repeatedly sliding said sheath forward over said bristled portion to urge the sample tissue from said bristled portion and into said liquid fixative.

16. The method of claim 11, further comprising:

sliding said sheath forward over said bristled portion to urge the sample tissue from said bristled portion and onto a slide.

17. A cervical sampler, comprising:

a brush assembly comprising an elongated shaft and a tapered bristled portion at a distal end of said shaft, said bristled portion configured for ectocervical sampling; and a sheath slidably disposed on said shaft, said sheath having a first position in which said sheath covers and compresses said bristled portion to reduce the insertion profile of said cervical sampler, and a second position in which said sheath exposes said bristled portion and permits said bristled portion to return to an uncompressed state;

wherein said sheath has an inside diameter which is smaller than an outside diameter of an ectocervical portion of said bristled portion.

18. The cervical sampler of claim 17, wherein said sheath has a tapered distal end.

19. The cervical sampler of claim 18, further comprising a radially extending flange located on said sheath proximal of said tapered distal end.

20. The cervical sampler of claim 17, further comprising a radially extending flange located on said sheath.

21. The cervical sampler of claim 17, wherein said bristled portion forms an endocervical portion distal of said ectocervical portion, said ectocervical portion having a larger average cross-sectional area than said endocervical portion.

22. The cervical sampler of claim 17, wherein said bristled portion forms an endocervical portion distal of said ectocervical portion, said ectocervical portion having finer, softer bristles than said endocervical portion.

23. The cervical sampler of claim 17, further comprising a sheath stop located on said shaft proximal to said sheath.

24. The cervical sampler of claim 23, wherein said sheath stop comprises a handle.

25. The cervical sampler of claim 23, wherein said sheath stop comprises a knob.

26. A method of obtaining sample tissue from the cervical canal of a patient with a sampling brush having a shaft and a bristled portion on the shaft, said method comprising:

covering said bristled portion of said sampling brush by sliding a sheath distally along said shaft and over said bristled portion;

inserting said sampling brush into the cervical canal until said bristled portion, covered by said sheath, is disposed within the cervical canal;

sliding said sheath proximally along said shaft to expose said bristled portion to operative contact with the cervical canal; and advancing said bristled portion proximally within the cervical canal to collect sample tissue from the cervical canal upon said bristled portion;

wherein said sheath further comprises a radially extending flange and inserting said sampling brush into the cervical canal comprises inserting said sampling brush until said flange is adjacent the proximal extent of the cervical canal.

* * * * *